(12) United States Patent
Capaldo et al.

(10) Patent No.: US 7,435,986 B2
(45) Date of Patent: *Oct. 14, 2008

(54) SYSTEM AND METHOD FOR DETECTING REPEATING DEFECTS IN A LIGHT-MANAGEMENT FILM

(75) Inventors: Kevin Patrick Capaldo, Mt. Vernon, IN (US); Mark Cheverton, Mechanicville, NY (US); Kevin George Harding, Niskayuna, NY (US); Robert Tait, Brighton, MI (US)

(73) Assignee: Sabic Innovative Plastics IP B.V. (NL)

( * ) Notice: Subject to any disclaimer, the term of this patent is extended or adjusted under 35 U.S.C. 154(b) by 0 days.

This patent is subject to a terminal disclaimer.

(21) Appl. No.: 11/609,605

(22) Filed: Dec. 12, 2006

(65) Prior Publication Data

US 2007/0083577 A1   Apr. 12, 2007

Related U.S. Application Data

(62) Division of application No. 10/710,708, filed on Jul. 29, 2004, now Pat. No. 7,199,386.

(51) Int. Cl.
*G01N 21/86* (2006.01)
*H01L 27/00* (2006.01)

(52) U.S. Cl. .................... 250/559.4; 250/208.1

(58) Field of Classification Search . 250/559.4–559.46, 250/559.11, 559.04, 559.05, 559.07, 559.08; 356/239.1, 237.2, 239.7, 239.8, 237.1, 239.2, 356/239.3; 209/523–526, 528; 26/70; 382/112, 382/141–152; 700/143
See application file for complete search history.

(56) References Cited

U.S. PATENT DOCUMENTS

| | | | | |
|---|---|---|---|---|
| 5,598,006 A * | 1/1997 | Stringa | ................. | 250/559.46 |
| 5,691,811 A * | 11/1997 | Kihira | .................... | 356/239.1 |
| 6,040,584 A * | 3/2000 | Liu et al. | ............... | 250/559.11 |
| 6,774,986 B2 * | 8/2004 | Laskowski | ................. | 356/71 |
| 6,960,777 B2 * | 11/2005 | Soar | ..................... | 250/559.11 |
| 7,030,400 B2 * | 4/2006 | Rivera et al. | ........... | 250/559.11 |

\* cited by examiner

*Primary Examiner*—Que T. Le
*Assistant Examiner*—Pascal M Bui-Pho
(74) *Attorney, Agent, or Firm*—Cantor Colburn LLP

(57) ABSTRACT

A system and a method for detecting defects in a light-management film are provided. The system includes a first light source configured to emit light onto a first side of the film in a first predetermined region of the film. The system further includes a second light source configured to emit light onto a second side of the film in the first predetermined region of the film. The system further includes a first camera configured to receive a first portion of light reflected from the first predetermined region of film from the first light source and a second portion of the light propagating through the film from the second light source. Finally, the system includes a signal-processing device openably coupled to the first camera configured to detect a defect in the first predetermined region of the film based on at least one of the first and second portions of light.

14 Claims, 8 Drawing Sheets

SYSTEM AND METHOD FOR DETECTING REPEATING DEFECTS IN A LIGHT-MANAGEMENT FILM

CROSS REFERENCE TO RELATED APPLICATIONS

This application is a divisional of U.S. Ser. No. 10/710,708, filed on Jul. 29, 2004.

BACKGROUND OF THE INVENTION

Diffusive light-management films, including light-diffusive films, diffusive light-angle management films, and diffusive reflective polarizing films have been developed for visual displays such as liquid crystal device (LCD) displays. During the manufacture of the diffusive light-management films, film defects can occur that need to be detected.

Machine vision systems have been developed for determining defects in non-diffusive films, such as transparent films. The system propagates light through the film and then monitors the propagated light to determine if defects exist in the film. These systems, however, may not be able to detect defects in diffusive light management films as the light diffusion blurs the image of the defect. For example, if a defect is on a bottom surface of a light-management film and light propagates through a bottom surface of the film and outwardly from a top surface of the film, the film would diffuse the light as it propagates through the film. Accordingly, a camera disposed proximate the top surface of the film may not be able to detect the defect on the bottom surface of the film due to the light diffusion through the film.

There is thus a need for an improved machine vision system that can effectively detect defects in a light-management film.

BRIEF DESCRIPTION OF THE INVENTION

A system for detecting non-repeating defects in a light management film in accordance with an exemplary embodiment is provided. The film has a first side and a second side. The system includes a first light source configured to emit light onto the first side of the film in a first predetermined region of the film. The system further includes a second light source configured to emit light onto the second side of the film in the first predetermined region of the film. The system further includes a first camera configured to receive a first portion of light reflected from the first predetermined region of film from the first light source and a second portion of the light propagating through the film from the second light source. Finally, the system includes a signal-processing device operably coupled to the first camera configured to detect a defect in the first predetermined region of the film based on at least one of the first and second light portions.

A method for detecting non-repeating defects in a light-management film having a first side and a second side, in accordance with another exemplary embodiment is provided. The method includes emitting light from a first light source onto the first side of the film in a first predetermined region of the film. The method further includes emitting light from a second light source onto the second side of the light-management film in the first predetermined region of the film. Finally, the method includes detecting a defect in the film based on at least one of a first portion of the light reflected from the first predetermined region of film from the first light source and a second portion of the light propagating through the film from the second light source.

A system for detecting repeating defects in a light-management film in accordance with another exemplary embodiment is provided. The film has a first side and a second side. The system includes first and second light source configured to emit light onto the first and second sides, respectively, of the film. The system further includes a first camera disposed adjacent the first side of the film proximate the first light source that receives transmissive and reflected light from the film and generates a first plurality of digital images of the film covering a first region of the film to a second region of the film as the film moves in an axial direction. The system further includes third and fourth light sources configured to emit light onto the first and second sides, respectively, of the film. The third light source emits light during a first predetermined time period when the fourth light source is not emitting light. The fourth light source emits light during a second predetermined time period after the first predetermined time period when the third light source is not emitting light. The system further includes a second camera disposed adjacent the second side of the film proximate the fourth light source that receives either transmissive or reflected light from the film and generates a second plurality of digital images of the film covering the first region of the film to the second region of the film as the film moves in the axial direction. Finally, the system includes a signal-processing device operably coupled to the first and second cameras configured to detect the repeating defect in the film based on the first and second plurality of digital images.

A method for detecting repeating defects in a light-management film having a first side and a second side in accordance with another exemplary embodiment is provided. The method includes moving the film past first and second light sources disposed proximate the first and second sides, respectively, of the film. The method further includes emitting light from the first and second light sources onto the first and second sides, respectively, of the film. The method further includes generating a first plurality of digital images of the film covering a first region of the film to a second region of the film using a first camera disposed adjacent the first side of the film that receives transmissive and reflected light from the film. The method further includes moving the film past third and fourth light sources disposed proximate the first and second sides, respectively, of the film. The method further includes emitting light from the third light source onto the first side for a first predetermined time period while not emitting light from the fourth light source and then emitting light from the fourth light source onto the second side for a second predetermined time period while not emitting light from the third light source. The method further includes generating a second plurality of digital images of the film covering the first region of the film to the second region of the film using a second camera disposed adjacent the second side of the film that receives either transmissive or reflected light from the film. Finally, the method includes detecting a repeating defect in the film based on the first and second plurality of digital images.

Other systems and/or methods according to the embodiments will become or are apparent to one with skill in the art upon review of the following drawings and detailed description. It is intended that all such additional systems and methods be within the scope of the present invention, and be protected by the accompanying claims.

DETAILED DESCRIPTION OF THE INVENTION

Figure 1:
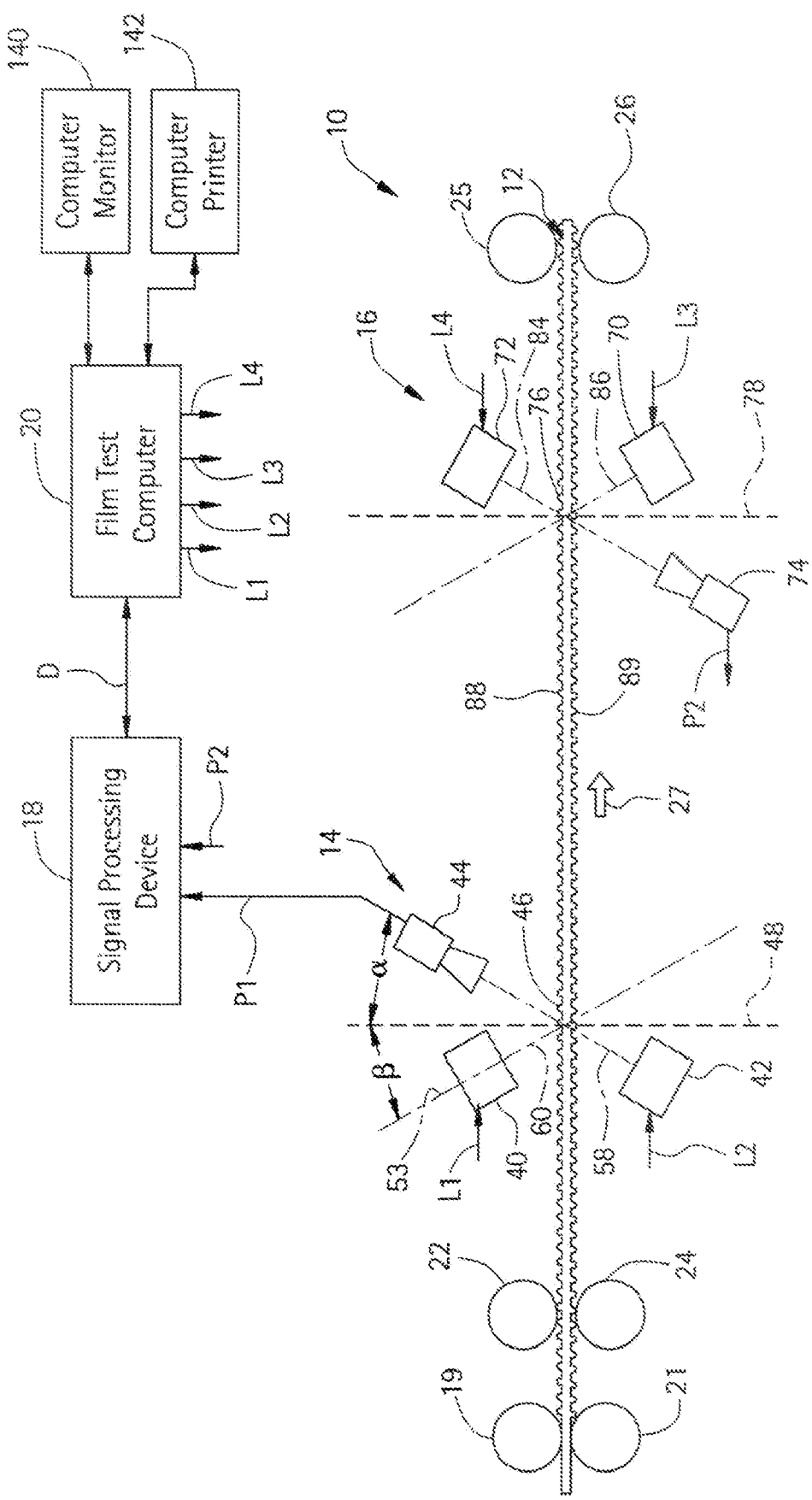
FIG. 1 is a schematic of a film monitoring system in accordance with an exemplary embodiment of the present invention.
Figure 2:
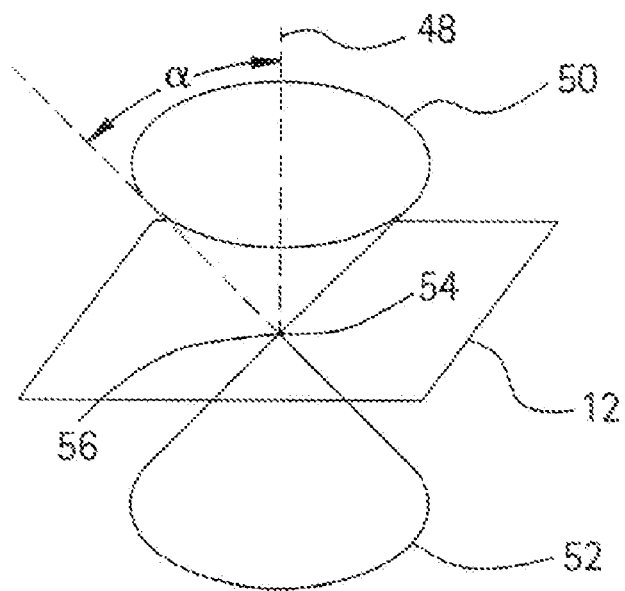
FIG. 2 is a schematic illustrating two conically shaped regions in which components of a first film monitoring station are disposed therein.
Figure 3:
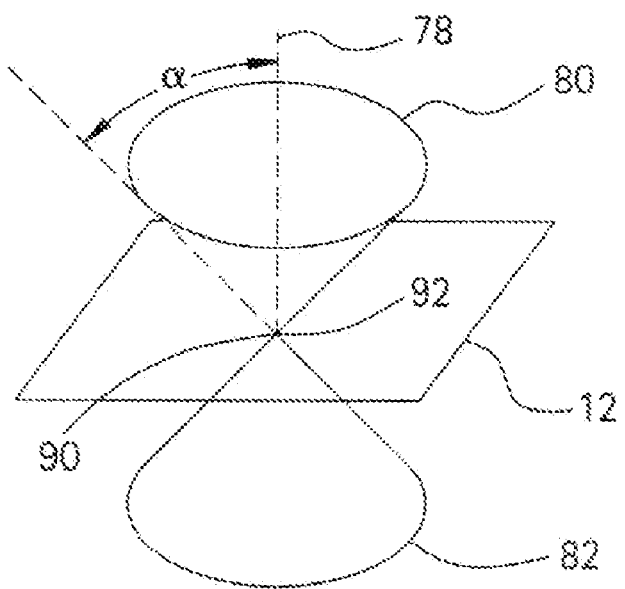
FIG. 3 is a schematic illustrating two conically shaped regions in which components of a second film monitoring station are disposed therein.

Referring to FIGS. 1 and 2, a film monitoring system 10 for detecting defects in a light-management film 12 is provided. The film monitoring system 10 includes a film monitoring station 14, a film monitoring station 16, a signal-processing device 18, a film test computer 20, rollers 19, 21, 22, 24 and feed rollers 25, 26. It should be noted that although the film monitoring system 10 includes two film monitoring stations, the film monitoring system 10 could include one or more film monitoring stations for detecting non-repeating defects and two or more film monitoring stations for detecting both non-repeating and repeating defects, as described below.

The rollers 19, 21 are provided to form a textured surface on at least one side of the film 12. The rollers 19, 21 are operably disposed proximate one another to receive a film 12 therebetween. The roller 19 has a textured surface that forms a textured surface on a first side of the film 12. The roller 21 has a substantially smooth surface for supporting the film 12 thereon. In an alternate embodiment, the roller 24 has a textured surface for forming a textured surface on a second side of the film 12.

The rollers 22, 24 are operably disposed proximate one another to receive the film 12 therebetween from the rollers 19, 21. The rollers 22, 24 are disposed downstream from the rollers 19, 21 and rotatably support and maintain a desired tension on the film 12 upstream of the film monitoring stations 14, 16. In an alternate embodiment, a motor (not shown) can be operably coupled to rollers 22, 24 to induce the rollers 22, 24 to urge the film 12 toward the film monitoring stations 14, 16.

The feed tools 25, 26 are operably disposed proximate one another to receive the film 12 therebetween after the film 12 has been scanned by the film monitoring stations 14, 16. The rollers 25, 26 are operably coupled to a motor (not shown) that rotates the rollers 25, 26 to rotatably support and to urge the film 12 to move pas the film monitoring stations 14, 16. The rollers 25, 26 maintain a desired tension on the film 12.

It should b e noted that in an alternate embodiment, one or more of the rollers 22, 24, 25, 26 could be replaced with other roller configurations to support the film 12 and to maintain a desired tension on the film 12, including S-wraps and conveying rollers for example.

The film monitoring station 14 is provided to detect defects in a film detection region 46 of the film 12. As shown, the film 12 moves via rollers 22, 24, 25, 26 in the direction of arrow 27 past the film monitoring station 14. The film monitoring station 14 generates digital images of the film 12 in a film detection region 46 that as transmitted to a signal-processing device 18. In particular, the film monitoring station 14 uses at least one of (i) a light beam 58 that passes through the film 12 and (ii) a reflected light beam 60 that reflects off of the film 12, to detect film defects. The film monitoring station 14 includes a light source 40, a light source 42, and a camera 44.

The camera 44 is provided to generate digital images of the film 12 which can be utilized by the signal-processing device 18 to detect defects in the film 12. The camera 44 comprises a change coupled device (CCD) camera that generates a digital image signal (P1) that is transmitted to the signal-processing device 18. In alternate embodiments, the camera 44 can comprise any camera that generates digital image signals of the film 12. The camera 44 is preferably disposed within a conically shaped region 50 above the film 12. The conically shaped region 50 extends from the film detection region 46 outwardly from a side 88 of the film 12 and has an apex 54 proximate the film detection region 46. The conically shaped region 50 is centered about an axis 48 that extends through the film detection region 46 generally perpendicular to the film 12. The conically shaped region 50 extends around the axis 48 at a predetermined angle ($\alpha$). The predetermined angle is within a range of 0-60 degrees. Of course, in alternate embodiments, the camera 44 could be disposed outside of the region 50. Further, the camera 44 is oriented to receive light from the film detection region 46. Still further, the inventors herein have empirically determined that the camera 44 can be adjusted slightly out of focus (e.g. 0-10% out of focus) to enhance the detection of defects in the film 12.

The light source 42 is provided to transmit a light beam 58 through the light-management film 12 at the film detection region 46 that is detected by the camera 44. The light source 42 comprises one or more of a light emitting device (LED), a halogen bulb, a fluorescent bulb, or other equivalent light source, which may or may not be strobed, that is controlled via a control signal (L2) received from the film test computer 20. The light source 42 is disposed within a conically shaped region 52 below the film 12. The conically shaped region 52 extends from the film detection region 46 outwardly from a side 89 of the film 12 and having an apex 56 proximate the film detection region 46. The conically shaped region 52 is centered about the axis 48 and extends around the axis 48 at the predetermined angle ($\alpha$). The predetermined angle is within the range of 0-60 degrees.

The light source 40 is provided to transmit a light beam 60 that is at least partially reflected off of the light-management film 12 at the film detection region 46 that is detected by the camera 44. The light source 40 comprises a light emitting device (LED), halogen, fluorescent, or other equivalent light source, which may or may not be strobed, that is controlled via a control signal (L1) received from the film test computer 20. The light source 40 is disposed within a conically shaped region 53 above the film 12. The conically shaped region 53 extends from the film detection region 46 outwardly from the side 89 of the film 12 and having an apex proximate the film detection region 46. The conically shaped region 53 is centered about the axis 48 and extends around the axis 48 at the predetermined angle (β). The predetermined angle (β) is defined by the following equation:

$$\beta = \alpha \pm 10°.$$

Both of the light sources 40 and 42 preferably illuminate the film 12 within an illumination uniformity range of five units on a 8-bit grayscale digital image.

The film monitoring station 16 is provided to detect defects in a film region 76 of the film 12. As shown, the film 12 moves via rollers 22, 24, 25, 26 in the direction of arrow 27 past the film monitoring station 16. The film monitoring station 16 generates digital images of the film 12 in a film detection region 76 that is transmitted to a signal-processing device 18. In particular, the film monitoring station 16 uses at least one of (i) a light beam 84 that passes through the film 12, and (ii) a light beam 86 that reflects off of the film 12, to detect film defects. The film monitoring station 16 includes a light source 70, a light source 72, and a camera 74.

The camera 74 is provided to generate digital images of the film 12 which can be utilized by the signal-processing device 18 to detect defects in the film 12. The camera 74 comprises a CCD camera that generates a digital image signal (P2) that is transmitted to the signal-processing device 18. In alternate embodiments, the camera 74 can comprise any camera that generates digital image signals of the film 12. The camera 74 is preferably disposed within a conically shaped region 82 below the film 12. The conically shaped region 82 extends from the film detection region 76 outwardly from a side 89 of the film 12 and has an apex 90 proximate the film detection region 76. The conically shaped region 82 is centered about an axis 78 that extends through the film detection region 76 generally perpendicular to the film 12. The conically shaped region 82 extends around the axis 78 at the predetermined angle (α). Of course, in alternate embodiments, the camera 74 could be disposed outside of the region 82. Further, the camera is oriented to receive light from the film detection region 76. Still further, the inventors herein have empirically determined that the camera 74 can be adjusted slightly out of focus to enhance the detection of defects in the film 12.

The light source 72 is provided to transmit a light beam 84 through the light-management film 12 that is detected by the camera 74. The light source 72 comprises one or more of a LED, a halogen bulb, a fluorescent bulb, or other equivalent light source, which may or may not be stored, that is controlled via a control signal (L4) received from the film test computer 20. The light source 72 is disposed within a conically shaped region 80 above the film 12. The conically shaped region 80 extends from the film detection region 76 outwardly from a side 88 of the film 12 and having an apex 92 proximate the film detection region 76. The conically shaped region 80 is centered about the axis 78 and extends around the axis 78 at the predetermined angle (α). The predetermined angle is within the range of 0-60 degrees.

The light source 70 is provided to transmit a light beam 86 that is at least partially reflected off of the light-management film 12 in the film detection region 76 that is detected by the camera 74. The light source 70 comprises one or more of a LED, a halogen bulb, a fluorescent bulb, or other equivalent light source, which may or may not be strobed, that is controlled via a control signal (L3) received from the film test computer 20. The light source 70 is disposed within a conically shaped region 82 below the film 12. The conically shaped region 82 extends from the film detection region 76 outwardly from the side 89 of the film 12 and having an apex proximate the film detection region 76. The conically shaped region 82 is centered about the axis 78 and extends around the axis 78 at the predetermined angle (β). The predetermined angle (β) is defined by the following equation:

$$\beta = \alpha \pm 10°.$$

The signal-processing device 18 is provided to receive digital image signals (P1) and (P2) and to detect defects within the film 12 based upon the digital image signals (P1) and (P2). When the signal-processing device 18 detects at least one defect in the film 12, the device 18 transmits a defect detection signal (D) to the film test computer 20 containing a coordinate location of the defect on the film 12. Of course, if more than one defect is detected, the device 18 would send a coordinate location for each detected defect on the film 12 to the film test computer 20. The signal-processing device 18 comprises a programmable machine vision circuit configured to detect defects within the film 12.

The film test computer 20 is operably coupled to the signal-processing device 18 and the light sources 40, 42, 70, and 72. The film test computer 20 is configured to control when the light sources 40, 42, 70, 72 emit light beams using control signs (L1), (L2), (L3), (L4), respectively. The film test computer 20 is further configured to receive the defect detection signal (D) and to display a defect message or report on a computer monitor 140 coupled to the film test computer 20. Alternately, the film test computer 10 could print a defect message or report using a compute printer 142.

The film 12 is a light-management film having at least one textured surface with a plurality of light management texture elements, comprising one or more of (i) random bumps, (ii) hemispherical dents or protrusions, and (iii) arrays of prismatic elements. As a light beam contacts the light management texture elements, the light beam is diffused or spread out as it passes through the film 12. Although a sheet of film 12 is moved past the monitoring stations 14 and 16 using rollers 22, 24, 25, 26, the film 12 could be presented to one or more film monitoring stations as individual segments of film cut to predetermined dimensions. In an alternate embodiment, the segments of film could be presented to the monitoring stations using other film handling devices other than the rollers 22, 24, 25 and 26.

Figure 4:
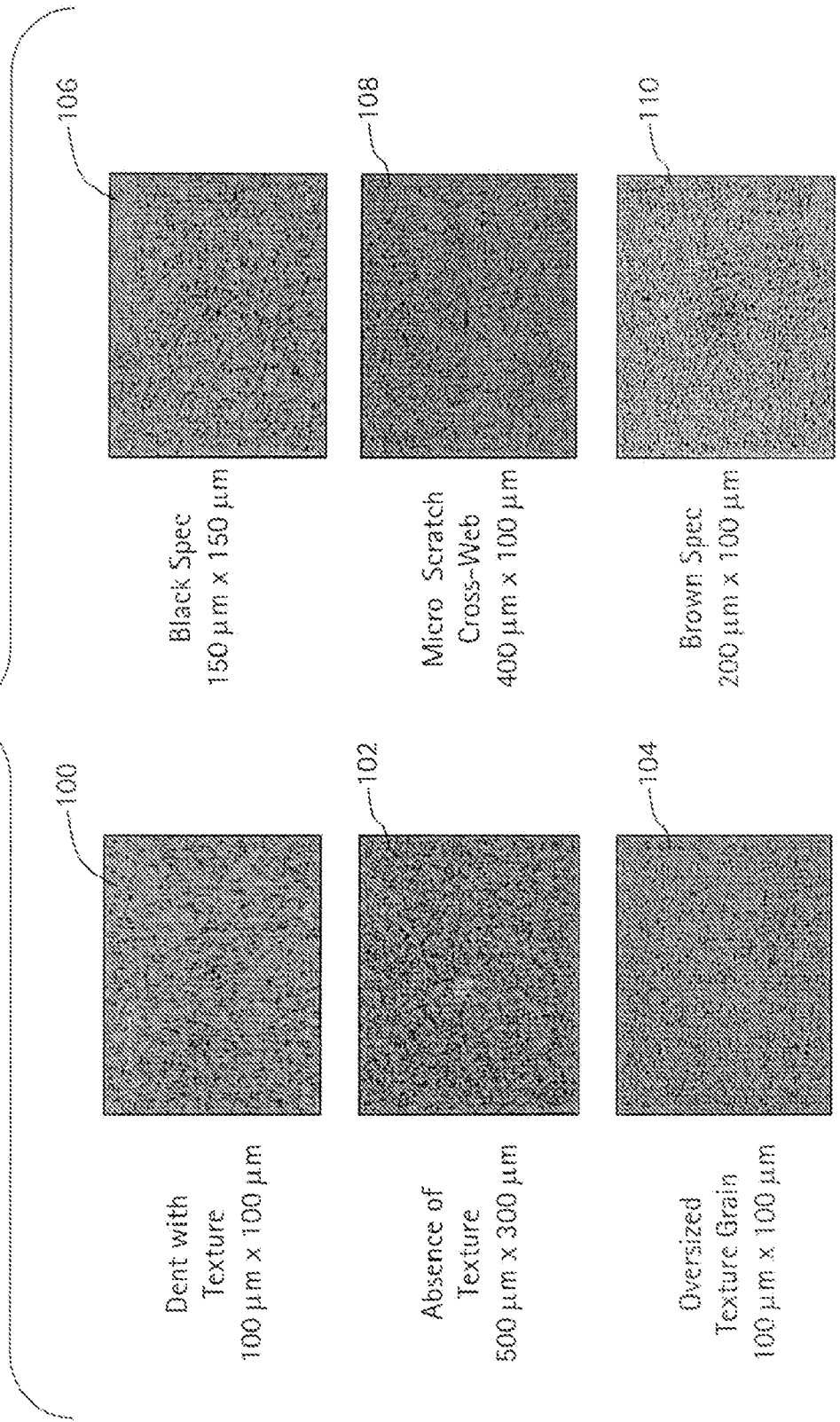
FIG. 4 is a schematic illustrating digital images containing film defects that are detected by the film monitoring system of FIG. 1.

Referring to FIG. 4, a brief description of the types of defects that can occur within the light-management film 12 and that are detected by the film monitoring system 10 will be described. In particular, the two common types of defects in the light-management film 12 are repeating defects and non-repeating defects.

Repeating defects are point defects formed on the film 12 due to a surface defect on one or more of the rollers 19, 21, 22, 24, 25, 26 or any other roller utilized to support or form the film 12. Repeating defects are reproduced in predetermined distance intervals on the film 12. For example, repeating defects include (i) textured dents on the film surface, (ii) an absence of texture on a region of the film surface, and (iii) oversized textured grain on the film surface. Repeating defects can occur when a rotating roller has a piece of dirt thereon and is contacting the film 12.

The digital image 100 illustrates a dented region in the film 12, comprising a repeating film defect. The digital image 100 is generated by one of the cameras 14, 16 and represents a digital image of the film 12 in a film detection region. The cameras can generate digital images identifying dented regions in the film 12 by utilizing a light beam that has propagated through the film 12.

The digital image 102 illustrates a region on the film 12 that does not have a textured surface, comprising a repeating film defect. The digital image 102 is generated by one of the cameras 14, 16 and represents a digital image of the film 12 in a film detection region. The cameras can generate digital images identifying regions on the film 12 that do not have a textured surface by utilizing a light beam that has been reflected from the film 12.

The digital image 104 illustrates a region on the film 12 that has an oversized textured grain on the film surface comprising a repeating film defect. The digital image 104 is generated by one of the cameras 14, 16 and represents a digital image of the film 12 in a film detection region. The cameras can generate digital images identifying oversized textured grain on a film 12 by utilizing a light beam that has been reflected from the film 12.

Non-repeating defects are any point defects on the film 12 that are not caused by the rollers. Non-repeating defects are generally caused by contamination of particles or gels within or on the film 12 and are not reproduced at predetermined distance intervals on the film 12. For example, non-repeating defects include (i) a black region on the film surface or in the film, (ii) a micro-scratch on the film surface, and (iii) a brown region on the film surface.

The digital image 106 illustrates a region on the film 12 that has a black region on the film 12, comprising a non-repeating film defect. The digital image 106 is generated by one of the cameras 14, 16 and represents a digital image of the film 12 in a film detection region. The cameras can generate digital images identifying black regions on the film 12 by utilizing either a light beam that has been reflected from the film 12 or a light beam that has propagated through the film 12.

The digital image 108 illustrates a region on the film 12 that has a micro-scratch on the film 12, comprising a non-repeating film defect. The digital image 108 is generated by one of the cameras 14, 16 and represents a digital image of the film 12 in a film detection region. The cameras can generate digital images identifying micro-scratches on the film 12 by utilizing either a light beam that has been reflected from the film 12 or a light beam that has propagated through the film 12.

The digital image 110 illustrates a region on the film 12 that has a brown region on the film 12, comprising a non-repeating film defect. The digital image 110 is generated by one of the cameras 14, 16 and represents a digital image of the film 12 in a film detection region. The cameras can generate digital images identifying brown regions on the film 12 by utilizing either a light beam that has been reflected from the film 12 or a light beam that has propagated through the film 12.

Figure 5:
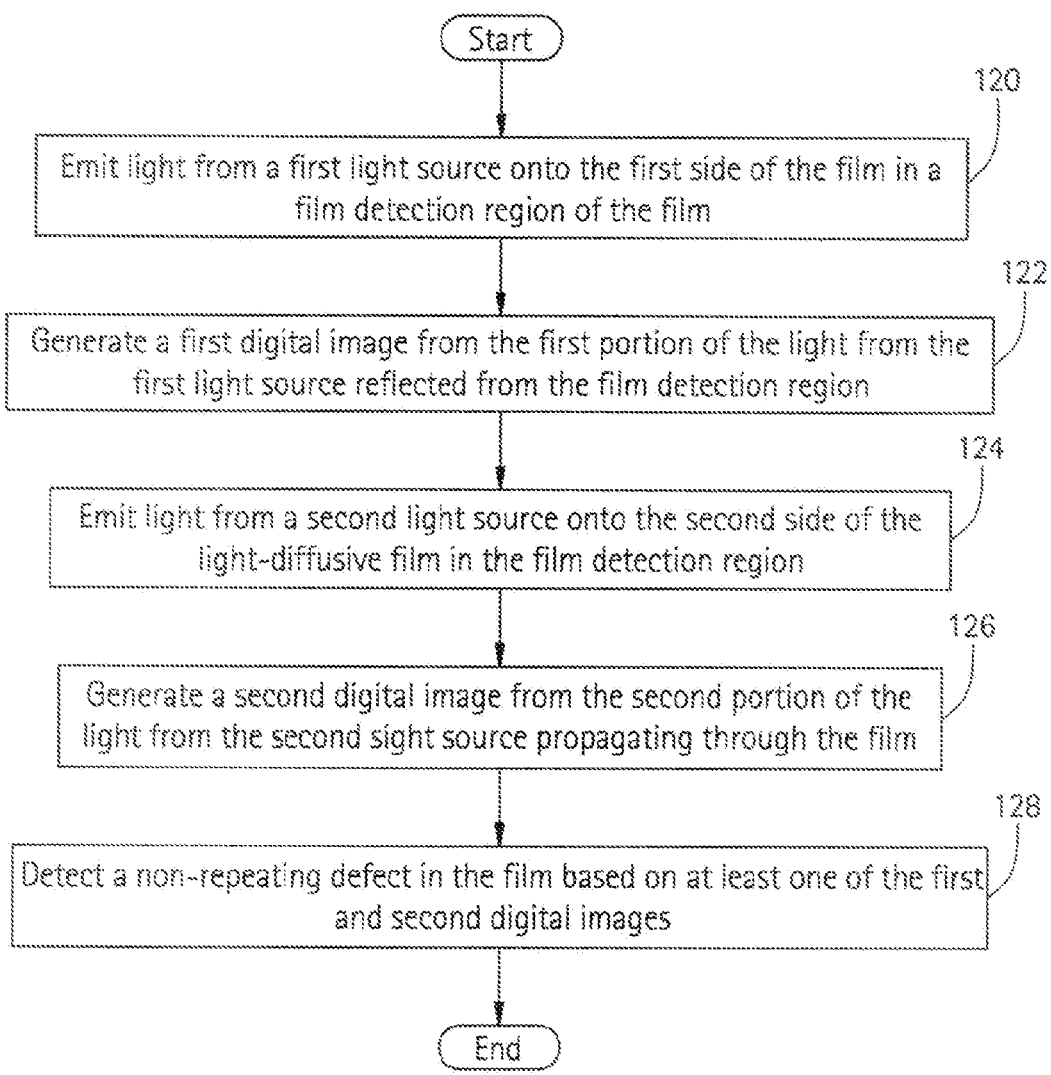
FIGS. 5 and 6 are flowcharts of a method for detecting non-repeating defects in a light-management film.
Figure 6:
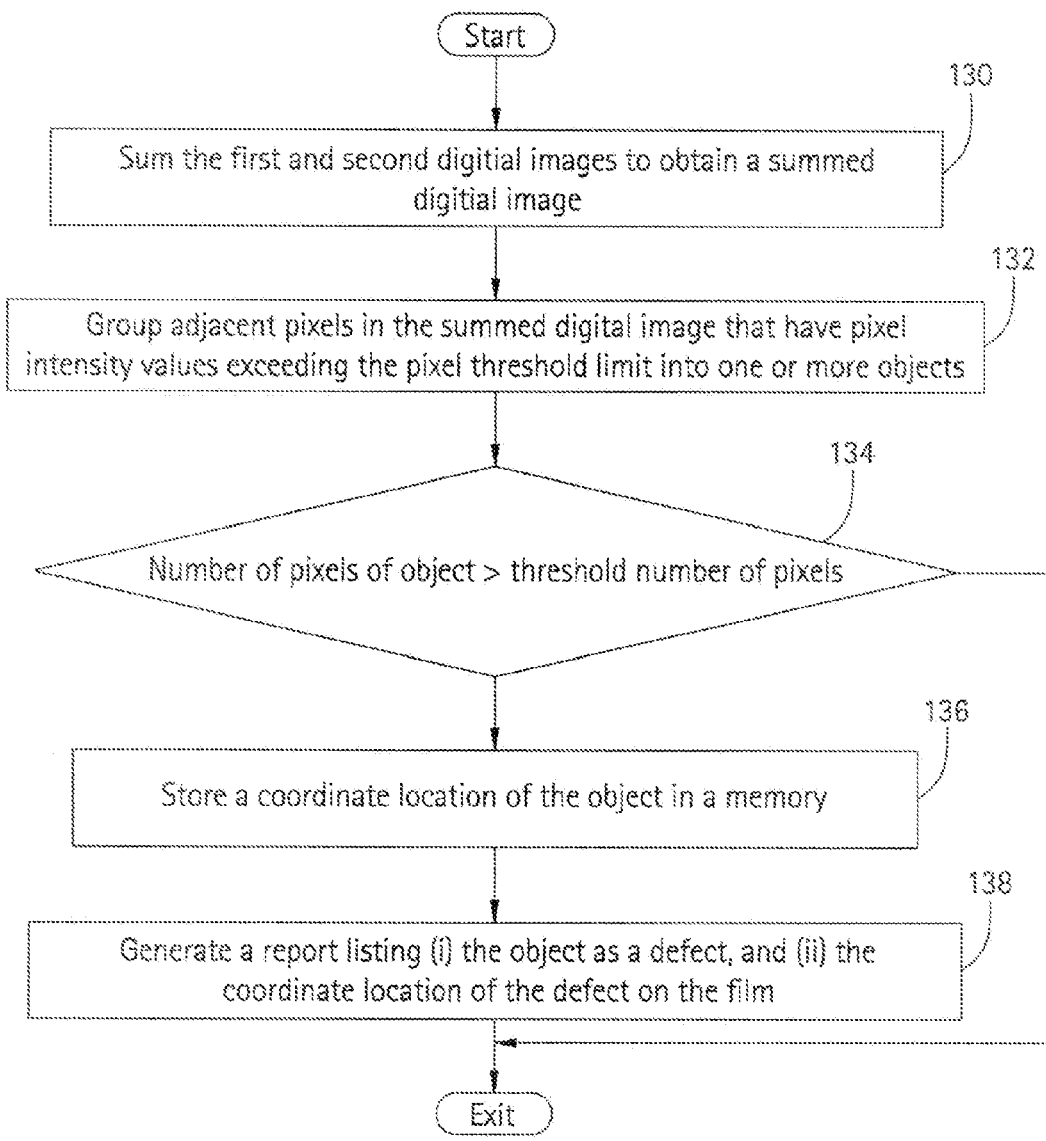
Figure 7:
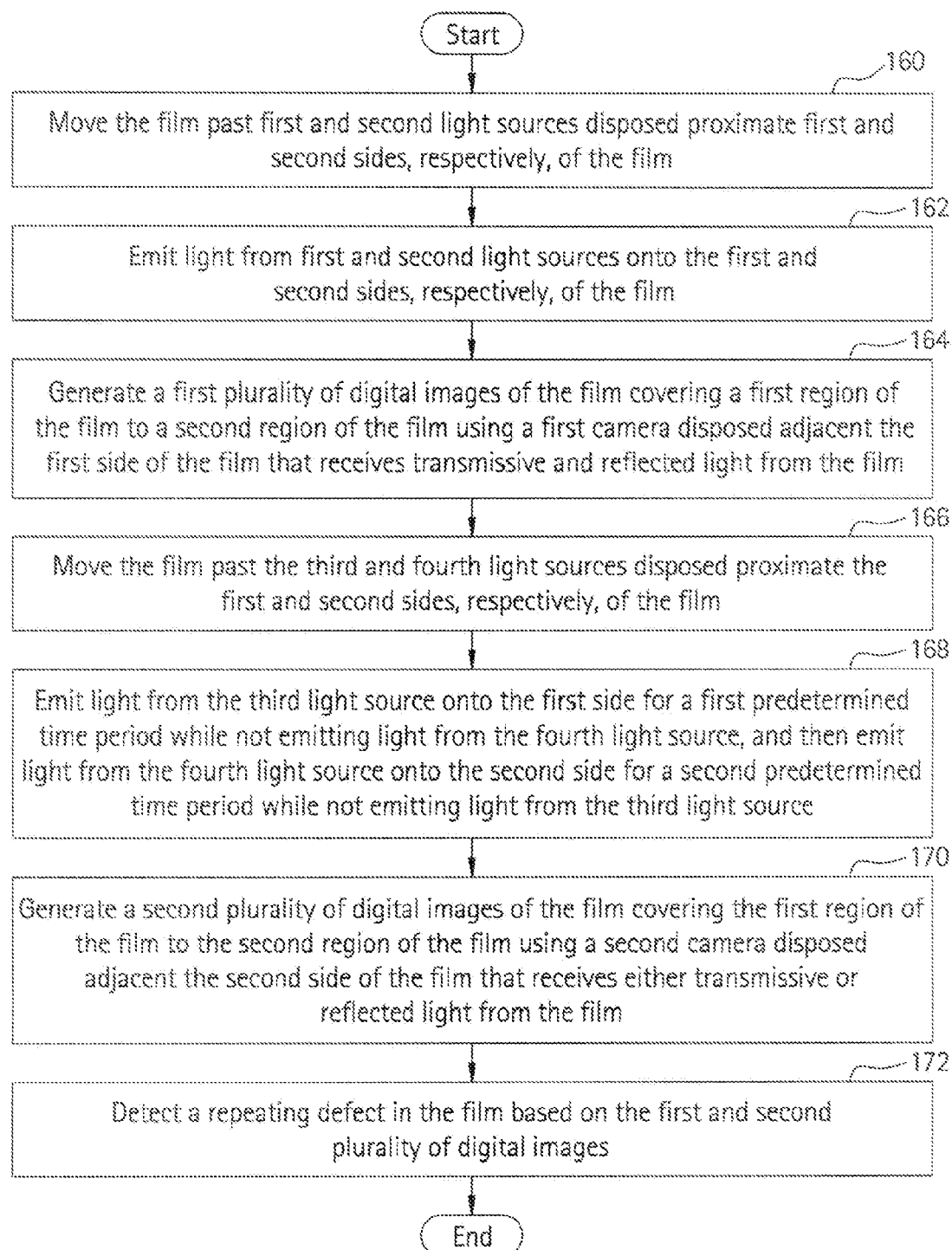
FIGS. 7 and 8 are flowcharts of a met hod for detecting repeating defects in a light-management film.

Referring to FIGS. 5 and 6, a method for detecting non-repeating defects in a light-management film 12 will now be described. The method will be described for use with the film monitoring station 14. However, the method can be utilized for each of a plurality of monitoring stations for detecting defects in the film 12.

At step 120, the film test computer 20 induces the light source 40 to emit a light beam onto a side 88 of the film 12 in the film detection region 46.

At step 122, the camera 44 generates a first digital image from a first portion of the light beam from the light source 40 reflected from the film detection region 46.

At step 124, the film test computer 20 induces the light source 42 to emit a light beam onto a side 89 of the film 12 in the film detection region 46.

At step 126, the camera 44 generates a second digital image from a second portion of the light beam from the light source 42 propagating through the film 12.

At step 128, the signal-processing device 18 detects a defect in the film 12 based on at least one of the first and second digital images. The step 128 is implemented utilizing steps 130-138 described below.

To aid in reduction of false positives while maintaining defect detectability, at step 130, the signal-processing device 18 decreases the intensity of the image, and then sums the first and second digital images to obtain a summed digital image. In particular, signal-processing device 18 sums each pixel in the first digital image with a corresponding pixel in the second digital image.

At step 132, the signal-processing device 18 groups adjacent pixels, or pixels within about 100 microns from one another, in the summed digital image that have pixel intensity values either greater than (bright defect) or less than (dark defect) a pixel threshold limit into one more objects.

At step 134, the signal-processing device 18 makes a determination as to whether the number of pixels of an object is greater than a threshold number of pixels, defining a defect. If the value of step 134 equals "yes", indicating a defect has been detected, the method advances to step 136. Otherwise, the method is exited.

At step 136, a coordinate location of the object is stored in a memory of film test computer 20.

At step 138, the film test computer 20 generates a report listing: (i) the object as a defect, and (ii) the coordinate location of the defect on the film 12. The report can be displayed on a computer monitor 140 attached to the film test computer 20 or can be printed using a printer 142.

Referring to FIGS. 7-11, a method for detecting repeating defects in a light-management film 12 will now be described. The method will be described for use with both film monitoring stations 14 and 16.

At step 160, the film 12 is moved past light sources 53, 58 disposed proximate sides 88, 89, respectively, of the film 12.

At step 162, the light sources 53, 58 emit light onto the sides 88, 89, respectively, of the film 12.

At step 164, the camera 44 generates a first plurality of digital images of the film 12 covering a first region 188 of the film to a second region 190 of the film 12 that receives transmissive and reflected light from the film 12. For example, referring to FIG. 9, the camera 44 can generate digital images 220, 222, 224 wherein the digital images 220, 222, 224 illustrate defects 196, 198, 200, respectively that are on the film 12.

At step 166, the film 12 moves past the light sources 72, 70 disposed proximate the sides 88, 89, respectively, of the film 12.

At step 168, the light source 72 emits light onto the side 88 for a first predetermined time period while the light source 70 does not emit light, and then the light source 70 emits light onto the side 89 for a second predetermined time period while the light source 72 odes not emit light. It should be noted that the step 168 is iteratively repeated while the film 12 is moving past the light sources 70, 72.

At step 170, the camera 74 generates a second plurality of digital images of the film 12 covering the first region 188 of the film to the second region 190 of the film 12 that receives either transmissive or reflected light from the film 12. For example, referring to FIG. 10, the camera 74 can generate digital images 226, 228, 230 wherein the digital images 226, 230 illustrate defects 202, 204, respectively that are on the film 12.

Figure 8:
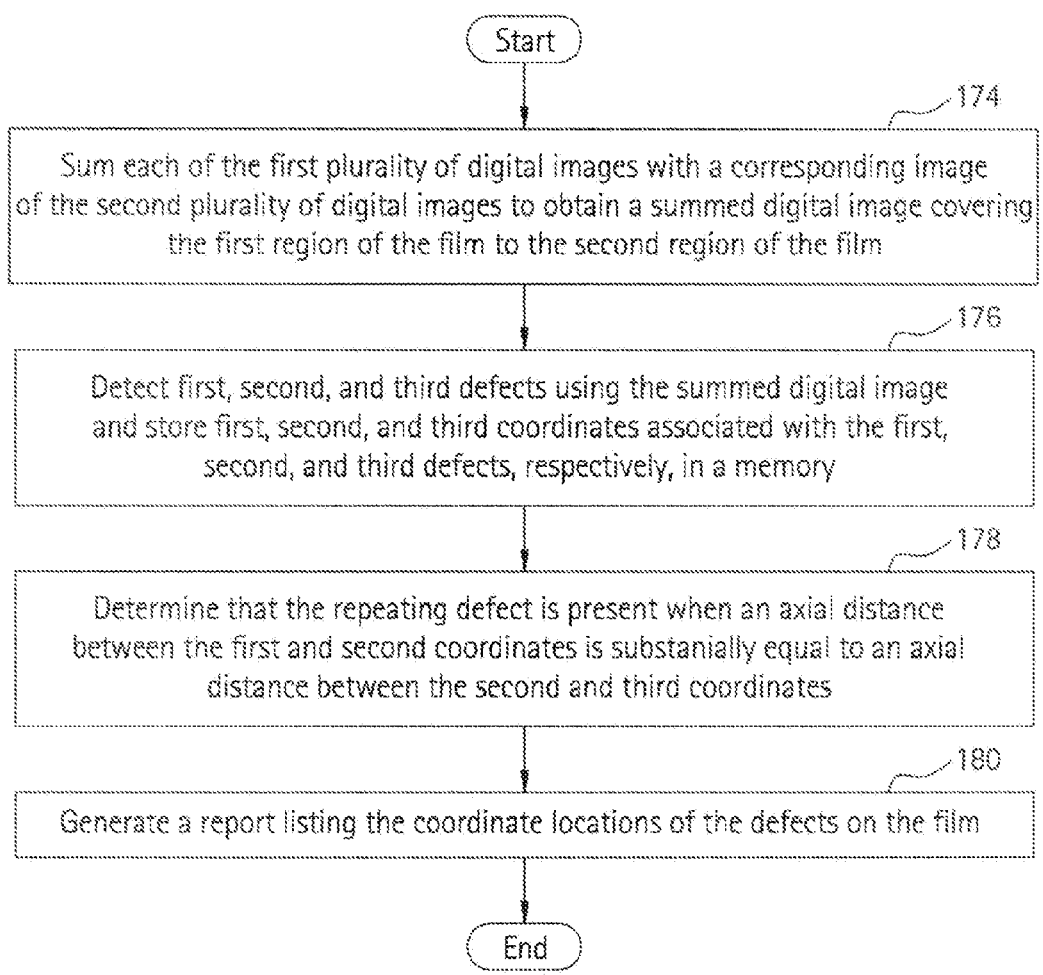
Figure 9:
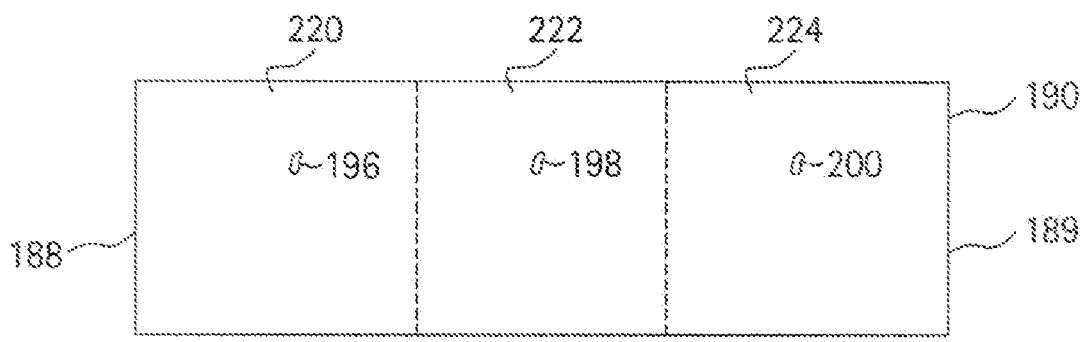
FIG. 9 is a schematic of a first plurality of digital images generated by a first camera of a first film monitoring station receiving both transmissive and reflected light from the film.
Figure 10:
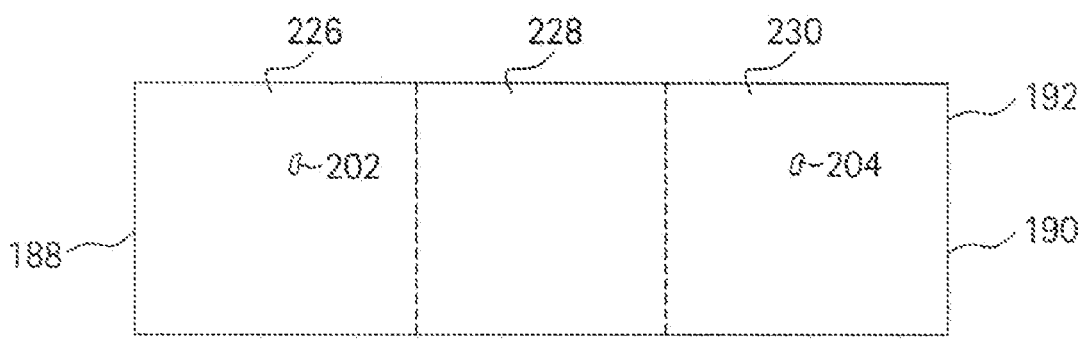
FIG. 10 is a schematic of a second plurality of digital images generated by a second camera of a second film monitoring station receiving either transmissive or reflected light form the film.
Figure 11:
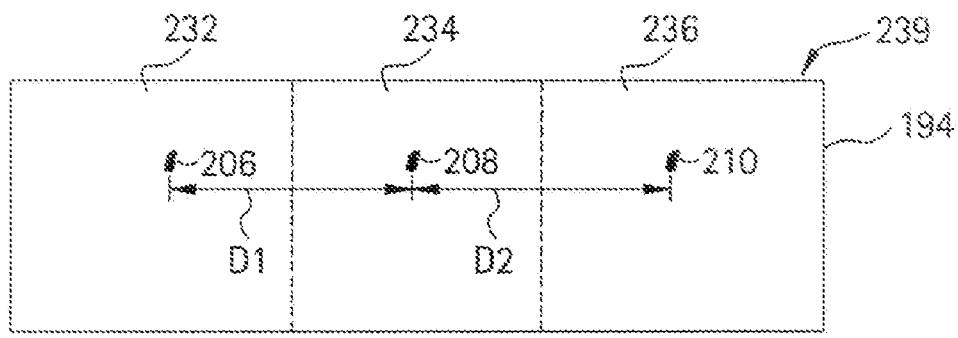
FIG. 11 is a schematic of a summed digital image obtained by summing a first plurality of digital images in FIG. 9 with the second plurality of digital images in FIG. 10.

Finally, at step 172, the signal-processing device 18 detects a repeating defect in the film 12 based on the first and second plurality of digital images. Referring to FIG. 8, the steps 174-180 for implementing step 172 are illustrated.

To aid in reduction of false positives while maintaining defect detectability, at step 174, the signal processing device 18 decreases the intensity of the image, and then sums each of the first plurality of digital images with a corresponding image of the second plurality of digital images to obtain a summed digital image covering the region 188 to the second region 190 of the film 12. For example, the signal-processing device 18 can sum the digital image 220 and the digital image 226 to obtain the digital image 232. Further, the signal-processing device 18 can sum the digital image 222 and the digital image 228 to obtain the digital image 234. Still further, the signal-processing device 18 can sum the digital image 224 and the digital image 230 to obtain the digital image 236. Each summed digital image can be inspected for defects.

At step 176, the signal-processing device 18 detects defects 206, 208, and 210 using the summed digital image 239 and stores first, second, and third coordinates associated with the defects 206, 208, 210, respectively, in a memory.

At step 178, the signal-processing device 18 determines that a repeating defect is present when an axial distance (D1) between the coordinates of defects 206 and 208 is substantially equal to an axial distance (D2) between the coordinates of defects 208 and 210 as well as the cross web distances of the defects being substantially equal.

At 180, the computer 20 generates a report listing the coordinate locations of the defects 206, 208, 210 on the film 12, and an indication that a repeating defect was detected.

During empirical observations, the foregoing method detected 88% of repeating defects. Further, the number of false positive detections of defects was less than or equal to 45 false positive detections for every 1000 summed digital images which covered 250 square inches of light management film.

The inventive system and methods for detecting both repeating and non-repeating defects in a light-management film represent a substantial advantage over other systems and methods. In particular, the system and methods have a technical effect of reliably detecting defects in the light-management film using at least one of a first light beam propagating through the film and a second light beam reflecting off of the film. In particular, the inventive system and methods can detect non-repeating defects such as flat surfaces on a textured film using reflected light from the film, and can detect defects such as dents or depressions with texture in the film using light which propagates through the film utilizing a film monitoring station 14. Still further, the system can detect repeating defects on the film using film monitoring stations 14, 16.

While the invention is described with reference to an exemplary embodiment, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. Moreover, the use of the term's first, second, etc. does not denote any order of importance, but rather the term's first, second, etc. are used to distinguish one element from another.

What is claimed is:

1. A system for detecting defects in a light-management film, the film having a first side and a second side, comprising:
   first and second light sources configured to emit light simultaneously onto the first and second sides, respectively, of a portion of the film;
   a first camera disposed adjacent the first side of the film proximate the first light source that receives transmissive and reflected light from the film and generates a first plurality of digital images of the film covering a first region of the film to a second region of the film as the film moves in an axial direction;
   third and fourth light sources configured to emit light onto the first and second sides, respectively, of the film, the third light source emitting light during a first predetermined time period when the fourth light source is not emitting light, the fourth light source emitting light during a second predetermined time period after the first predetermined time period when the third light source is not emitting light;
   a second camera disposed adjacent the second side of the film proximate the fourth light source that receives either transmissive or reflected light from the film and generates a second plurality of digital images of the film covering the first region of the film to the second region of the film as the film moves in the axial direction; and
   a signal-processing device operably coupled to the first and second cameras configured to detect the at least one defect in the film based on the first and second plurality of digital images, the signal processing device further configured to indicate that a repeating defect was detected based on the at least one defect being reproduced at predetermined intervals in the film.

2. The system of claim 1, wherein the first camera is disposed at least partially within a first conically shaped region, the first conically shaped region extending from the first predetermined region of film outwardly from the first side and having an apex proximate the first predetermined region, the first conically shaped region being centered about a first axis, the axis extending through the first predetermined region of film generally perpendicular to the film, the first conically shaped region extending around the first axis at a predetermined angle.

3. The system of claim 2, wherein the predetermined angle is within a range of 0 to 60 degrees.

4. The system of claim 2, wherein the second light source is disposed at least partially within a second conically shaped region, the second conically shaped region extending from the first predetermined region of film outwardly from the second side and having an apex proximate the first predetermined region, the second conically shaped region being centered about the first axis, the second conically shaped region extending around the first axis at the predetermined angle.

5. The system of claim 4, wherein the predetermined angle is within a range of 0 to 60 degrees.

6. The system of claim 4, wherein the first light source is disposed at least partially within a third conically shaped region, the third conically shaped region extending from the first predetermined region of film outwardly from the first side and having an apex proximate the first predetermined region, the third conically shaped region being centered about the first axis, the third conically shaped region extending around the first axis at a second angle.

7. The system of claim 6, wherein the second angle is within a range of 0 to 60 degrees.

8. A method for detecting repeating defects in a light-management film having a first side and a second side, the method comprising:
   moving the film past first and second light sources disposed proximate the first and second sides, respectively, of the film;
   emitting light simultaneously from the first and second light sources onto the first and second sides, respectively, of a portion of the film;
   generating a first plurality of digital images of the film covering a first region of the film to a second region of the film using a first camera disposed adjacent the first side of the film that receives transmissive and reflected light from the film;

moving the film past a third light source and a fourth light source disposed proximate the first and second sides, respectively, of the film;

emitting light from the third light source onto the first side for a first predetermined time period while not emitting light from the fourth light source and then emitting light from the fourth light source onto the second side for a second predetermined time period while not emitting light from the third light source;

generating a second plurality of digital images of the film covering the first region of the film to the second region of the film using a second camera disposed adjacent the second side of the film that receives either transmissive or reflected light from the film;

detecting at least one defect in the film based on the first and second plurality of digital images; and indicating that a repeating defect was detected based on the at least one defect being reproduced at predetermined distance intervals in the film.

9. The method of claim 8, wherein the first camera is disposed at least partially within a first conically shaped region, the first conically shaped region extending from the first predetermined region of film outwardly from the first side and having an apex proximate the first predetermined region, the first conically shaped region being centered about a first axis, the axis extending through the first predetermined region of film generally perpendicular to the film, the first conically shaped region extending around the first axis at a predetermined angle.

10. The method of claim 9, wherein the predetermined angle is within a range of 0 to 60 degrees.

11. The method of claim 9, wherein the second light source is disposed at least partially within a second conically shaped region, the second conically shaped region extending from the first predetermined region of film outwardly from the second side and having an apex proximate the first predetermined region, the second conically shaped region being centered about the first axis, the second conically shaped region extending around the first axis at the predetermined angle.

12. The method of claim 11, wherein the predetermined angle is within a range of 0 to 60 degrees.

13. The method of claim 11, wherein the first light source is disposed at least partially within a third conically shaped region, the third conically shaped region extending from the first predetermined region of film outwardly from the first side and having an apex proximate the first predetermined region, the third conically shaped region being centered about the first axis, the third conically shaped region extending around the first axis at a second angle.

14. The method of claim 13, wherein the second angle is within a range of 0 to 60 degrees.

* * * * *